(12) United States Patent
Kawabe

(10) Patent No.: US 7,864,922 B2
(45) Date of Patent: Jan. 4, 2011

(54) WAVELENGTH-DISPERSIVE X-RAY SPECTROMETER

(75) Inventor: Kazuyasu Kawabe, Tokyo (JP)

(73) Assignee: JEOL Ltd., Tokyo (JP)

( * ) Notice: Subject to any disclaimer, the term of this patent is extended or adjusted under 35 U.S.C. 154(b) by 1048 days.

(21) Appl. No.: 11/514,689

(22) Filed: Sep. 1, 2006

(65) Prior Publication Data

US 2010/0284513 A1    Nov. 11, 2010

(30) Foreign Application Priority Data

Sep. 1, 2005  (JP)  ............................. 2005-253658
May 24, 2006  (JP)  ............................. 2006-143803

(51) Int. Cl.
*G21K 1/06*  (2006.01)
(52) U.S. Cl. ............................... 378/84; 378/70; 378/71
(58) Field of Classification Search .................. 378/44, 378/45, 70, 71, 84, 85, 145
See application file for complete search history.

(56) References Cited

U.S. PATENT DOCUMENTS 3,439,163  A    4/1969   De Jongh

FOREIGN PATENT DOCUMENTS

JP    52-027695    3/1977
JP    10-239495    9/1998

*Primary Examiner*—Courtney Thomas
(74) *Attorney, Agent, or Firm*—The Webb Law Firm

(57) ABSTRACT

An X-ray spectrometer which uses at least one curved analyzing crystal and which provides improved wavelength resolution of characteristic X-rays used for analysis and improved ratio of characteristic X-rays to background intensity by using only effective diffractive regions of the analyzing crystal. X-ray blocking plates upstand from an end of a crystal support member supporting the analyzing crystal in the direction of angular dispersion of the crystal toward the inside of a Rowland circle. Incident X-rays going from the point X-ray source toward the crystal and X-rays diffracted by the crystal toward an X-ray detector are partially blocked by the X-ray blocking plates. The shielded regions vary according to the incident angle $\theta$ of the incident X-rays. Optimum or nearly optimum effective regions of the surface of the crystal can be used at all times.

9 Claims, 11 Drawing Sheets

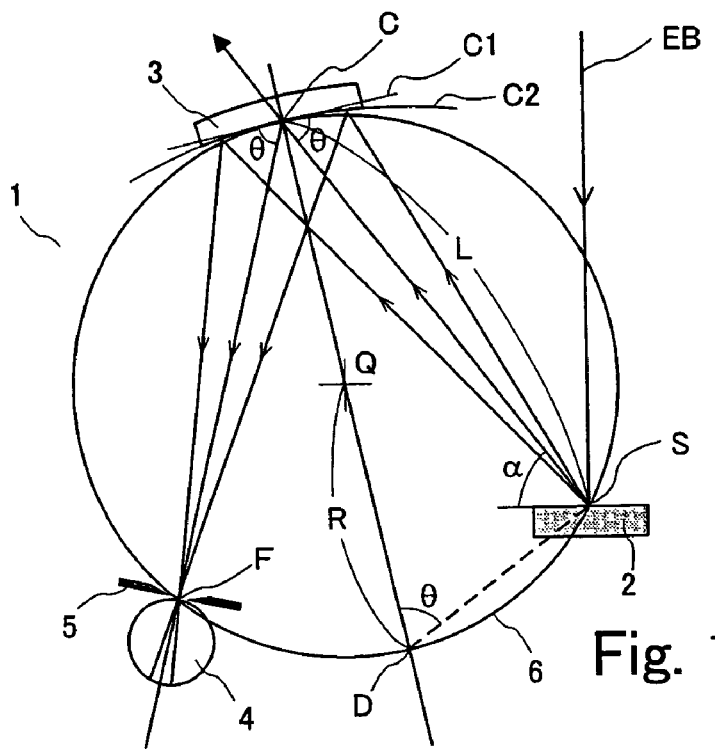
PRIOR ART
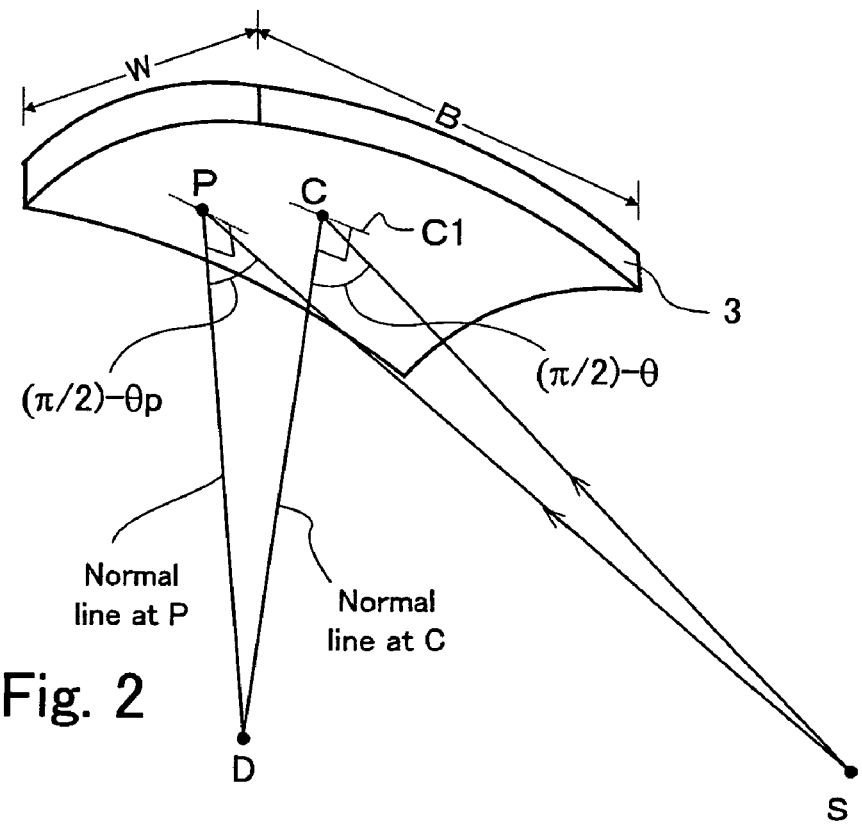

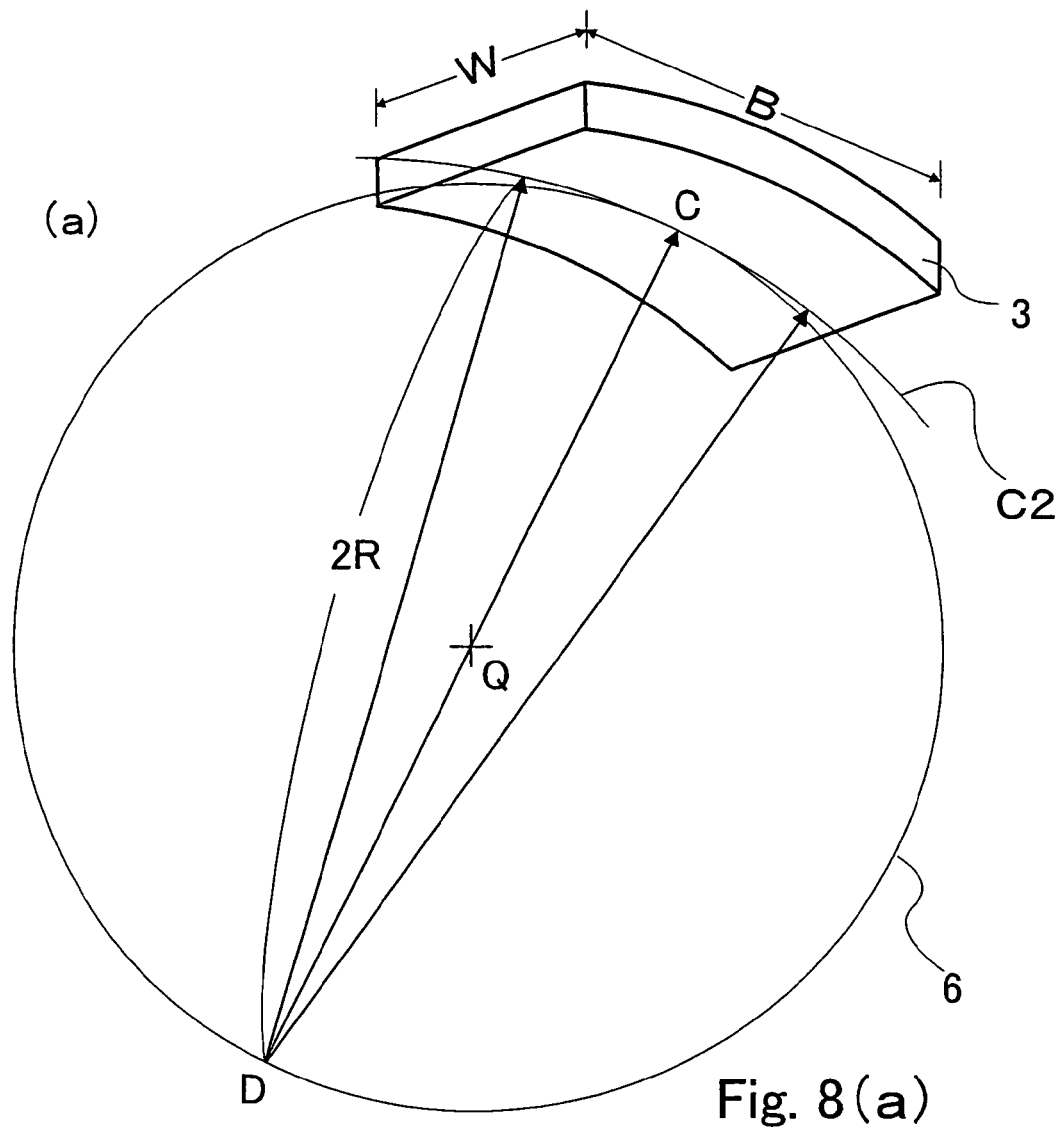
(a)
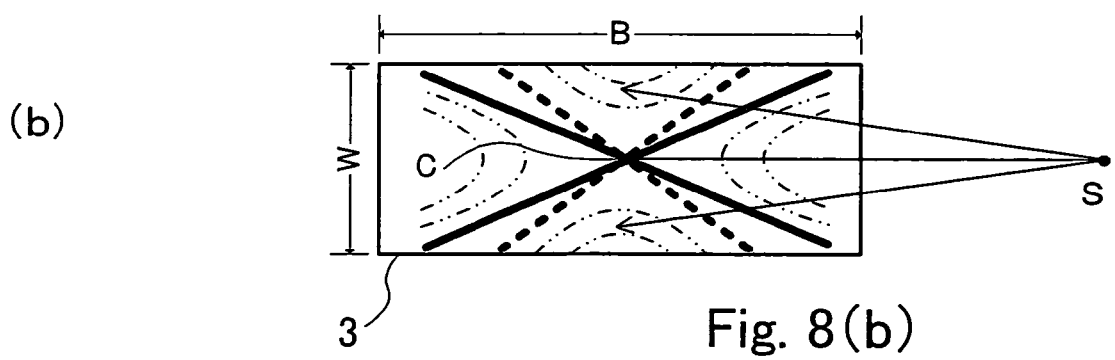
Fig. 8(a)
Fig. 8(b)

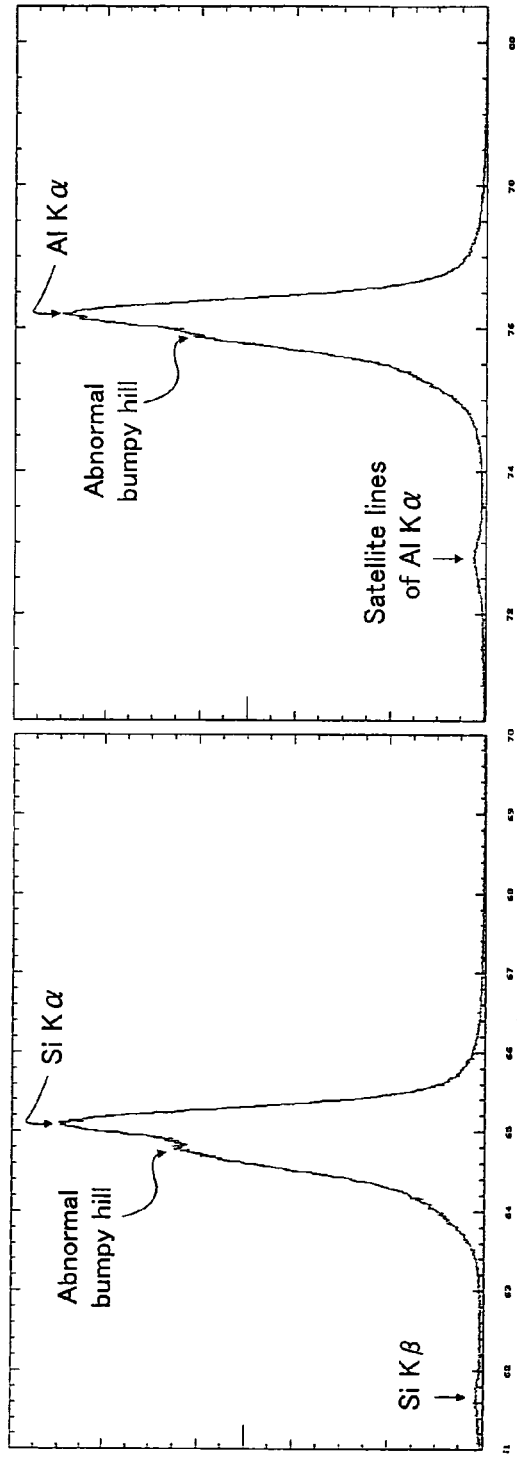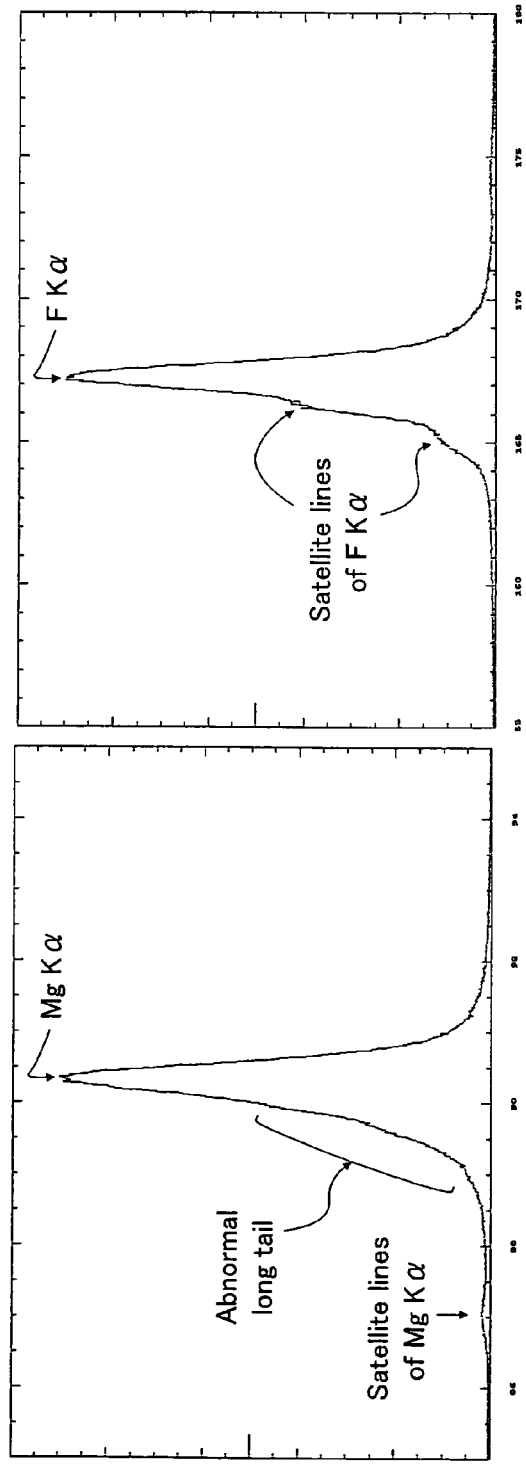

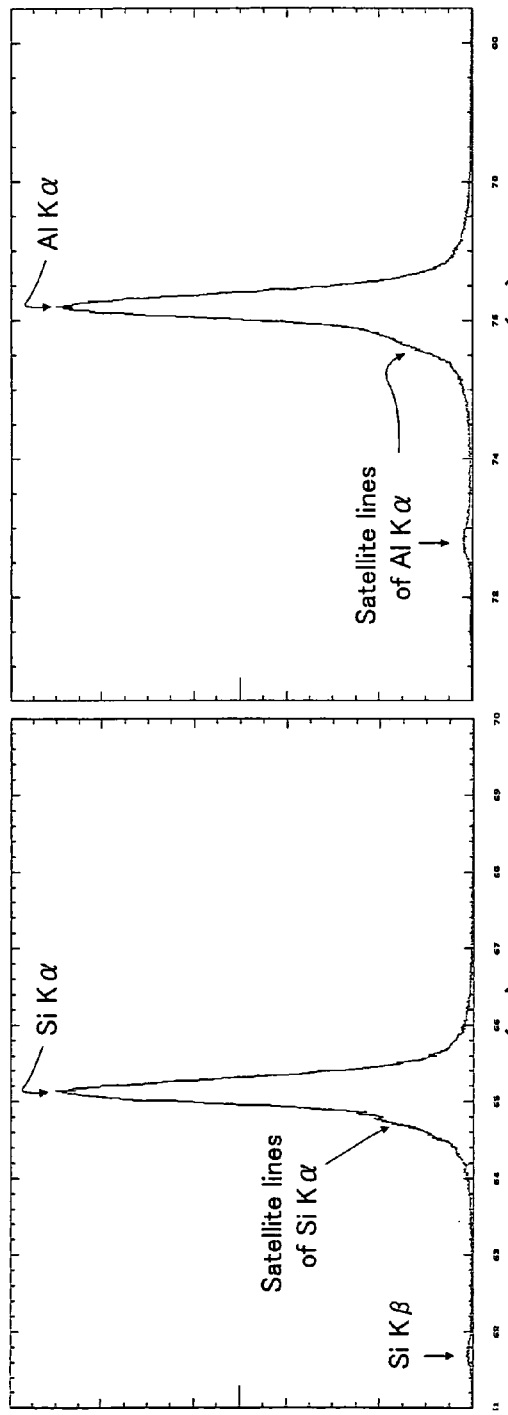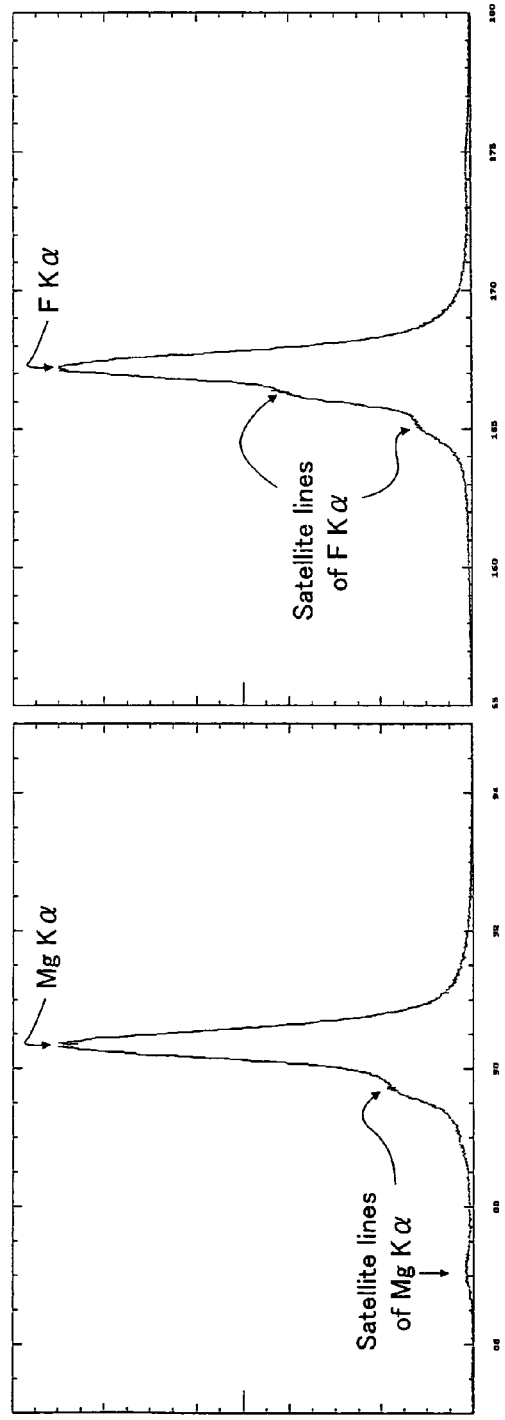

WAVELENGTH-DISPERSIVE X-RAY SPECTROMETER

BACKGROUND OF THE INVENTION

1. Field of the Invention

The present invention relates to a wavelength-dispersive X-ray spectrometer used in an electron probe microanalyzer (EPMA) or other similar instrument and, more particularly, to a technique for improving the performance of an X-ray spectrometer equipped with analyzing crystals curved in the direction of angular dispersion.

2. Description of Related Art

EPMAs are widely used as instruments for qualitatively and quantitatively analyzing a sample by sharply focusing an accelerated electron beam, directing the beam toward a surface of the sample, dispersing the generated characteristic X-rays, and analyzing the sample from the wavelengths and intensities of the dispersed X-rays. Generally, an EPMA is equipped with a wavelength-dispersive (WD) spectrometer designed to collect X-rays while moving the crystal along a straight path. This X-ray spectrometer may be hereinafter referred to as the WD spectrometer of the straight moving ray-collection type. Fundamental instrumentation of such an X-ray spectrometer is shown in the cross section of FIG. 1. When a focusing electron beam EB hits a sample 2, X-rays are produced. Electron optics for generating, accelerating, and focusing the electron beam EB are not shown.

An X-ray spectrometer 1 holds an analyzing crystal 3 whose center C moves on a straight line SC that is tilted at an angle of an X-ray takeoff angle α from a point of source S of X-rays. At this time, the point of source S, the center C of the analyzing crystal 3, and the center F of a slit 5 in an X-ray detector 4 are always present on the circumference of a Rowland circle 6 having a constant radius R. The position of the X-ray detector 4 and the center Q of the Rowland circle 6 move such that line segments SC and CF are kept equal in length. The curved crystalline lattice plane of the analyzing crystal 3 that extends along arc C2 always faces the center Q of the Rowland circle. The curved crystalline lattice plane is curved about a point D with a curvature of 2R. The point D is the intersection of an extension of a straight line CQ and the Rowland circle 6, the straight line CQ connecting the center C of the analyzing crystal 3 and the center Q of the Rowland circle 6. The length of the line segment SC is referred to as a spectral position L. Let θ be the angle of incidence of X-rays on the center C of the analyzing crystal. The angle θ is made between straight lines C1 and SC. The straight line C1 passes through the center C of the analyzing crystal and is tangent to the Rowland circle 6. The spectral position L is given by $$L = 2R \cdot \sin\theta \quad (1)$$

Meanwhile, from the Bragg condition, the diffraction conditions for the analyzing crystal are given by $$2d \cdot \sin\theta = n \cdot \lambda \quad (2)$$

where n is the order of diffraction and a positive integer, λ is the wavelength of X-rays, and d is the lattice spacing of the analyzing crystal. From Eqs. (1) and (2), we can obtain:

$$L = \frac{2R}{2d} \cdot n \cdot \lambda \quad (3)$$

It is possible to know the wavelength γ of the diffracted characteristic X-rays by measuring the spectral position L. Since the characteristic X-rays have a wavelength intrinsic to the element, the element contained in the sample can be identified. Furthermore, the concentration of the element contained in the sample can be known from the measured intensity of the characteristic X-rays.

Curved analyzing crystals have two types: Johansson type and Johann type. The differences between the Johansson and Johann types are shown in FIGS. 7(a) and 7(b) and FIGS. 8(a) and 8(b). FIG. 7(a) is a perspective view of a Johansson analyzing crystal, as viewed from inside a Rowland circle. First, the flat crystal is curved about a point D with curvature 2R such that the direction of angular dispersion of the analyzing crystal agrees with arc C2. Then, the curved crystal is polished with the same curvature R as the radius of the Rowland circle 6. Thus, X-rays incident on an arc of the analyzing crystal 3 in contact with the circumference of the Rowland circle 6 are diffracted while completely satisfying the requirement of Eq. (2) as shown in FIG. 7(b). However, the condition of Eq. (2) is satisfied less with going away from the arc in contact with the Rowland circle in a lateral direction perpendicular to the direction of angular dispersion. The double-dot-dash lines in FIG. 7(b) indicate positions with equal incident angle error. The double-dot-dash lines are referred to as equal incident-angle error lines. This tendency becomes more conspicuous with reducing the incident angle θ. Consequently, the wavelength resolution of the detected X-rays and the ratio of the intensity of the characteristic X-rays to the background intensity are deteriorated. Techniques for alleviating these problems are shown in Japanese Patent Laid-Open No. H10-239495.

The diffractive surfaces of Johansson crystals are physically polished. Therefore, some analyzing crystals for relatively long wavelengths have deteriorated performance and thus cannot be easily put into practical use. In this case, the following Johann type is used. FIG. 8(a) is a perspective view of an analyzing crystal in a Johann geometry, as viewed from the inside of a Rowland circle. In the Johann type, the direction of angular dispersion of the analyzing crystal is curved with curvature 2R about a point D such that the crystalline lattice plane extends along an arc C2. Under this curved condition, the crystal is used. In this type of analyzing crystal, X-rays incident on mutually crossing lines about the center C of the analyzing crystal are diffracted while completely satisfying Eq. (2) as shown in FIG. 8(b). Solid lines or dashed lines in FIG. 8(b) like the letter X expand in the direction of angular direction according to increasing the value of the incident angle θ. The double-dot-dash lines in FIG. 8(b) indicate positions with equal incident-angle error. The double-dot-dash lines are referred to as equal incident-angle error lines. The geometry of the mutually crossing lines varies with the value of L. As the incident angle θ decreases, the geometry approaches the center C of the analyzing crystal as shown as dashed lines in FIG. 8(b). Where it is difficult to polish the surface of an analyzing crystal or deterioration of performance with polishing should be avoided, a Johann geometry is used. LB (Langmuir-Blodgett) films often used as an analyzing element for X-ray spectroscopy for analysis of ultralight elements and analyzing elements using layered synthetic microstructures are difficult to polish and, therefore, they are used only in Johann geometry. Organic crystals synthetically produced from RAP (Rubidium acid phthalate), TAP (Thallium acid phthalate), or PET (Pentaerythritol) can be polished to make Johansson crystals, but they are often used to make Johann crystals because of a compromise with performance deterioration. A layered synthetic microstructure is created by artificially stacking a layer of high X-ray scattering capabilities and a spacer layer for securing lattice spacing on a substrate alternately. This microstructure is also referred to as an artificial superlattice. Analyzing elements of LB films and layered synthetic microstructures are not crystals in proper meaning but they are herein conveniently referred to as analyzing crystals.

An analyzing crystal is curved such that larger parts of X-rays emitted from a point X-ray source S are diffracted. However, both Johansson and Johann crystals of FIGS. 7(a) and 7(b) and FIGS. 8(a) and 8(b), respectively, are curved in only the direction of angular dispersion. In this case, the opening of the slit 5 in the X-ray detector 4 needs to have a length of 2W in a direction parallel to the widthwise direction of the analyzing crystal 3 as shown in FIG. 9. However, there is the problem that spatial restrictions are inevitably imposed when a wide slit is placed. Especially, the Johann analyzing crystal is affected greatly by limitation on the length of the slit, because the completely diffracted region is an X-shaped form and thus the width of the analyzing crystal can be increased with desirable results. In an attempt to avoid this problem and to obtain a high-intensity X-ray spectrometer, a two-directional curved analyzing crystal that is curved even in the widthwise direction of a Johann analyzing crystal has been fabricated. A two-directionally curved analyzing crystal having spherically-curved concave surfaces both in the direction of angular dispersion of the curved analyzing crystal and in a direction perpendicular to the direction of angular dispersion is herein referred to as a spherically-curved, Johann-type analyzing crystal, the concave surfaces having the same curvature as the diameter of the Rowland circle.

In a curved analyzing crystal fitted to an X-ray spectrometer mounted in an EPMA, the effective diffraction area actually contributing to diffraction differs depending on whether it is a Johansson or Johann crystal, on the spectral position L, and on the kind of analyzing crystal used. In some cases, the effective diffraction area is only about a half of the total area of the analyzing crystal.

The aforementioned spherically-curved Johann analyzing crystal has an optimum angular dispersion direction length according to the wavelength of the selected X-ray. That is, the length in the direction of angular dispersion is relatively small for shorter wavelengths of X-rays. The length in the direction of angular dispersion is relatively large for longer wavelengths of X-rays. Therefore, a spherically-curved, Johann-type analyzing crystal fabricated to match the length suitable for one wavelength of characteristic X-rays of interest within the analyzed range cannot be suitably used for spectral analysis of other characteristic X-rays which are widely different in wavelength from the X-ray to be selected. For example, the spectral waveform of the characteristic X-rays at wavelengths shorter than the X-rays to be spectrally selected has a tail on the lower diffraction angle side (on the shorter wavelength side), deteriorating the wavelength resolution. In very bad cases, lumpy hills appear on the waveform. This may impair the reliability of the waveform itself. Furthermore, there is the problem that the total area of the analyzing crystal is narrower than the effective diffraction area for characteristic X-rays longer than the X-rays to be spectrally selected, giving rise to a loss of the detectable X-ray intensity.

In an ordinary curved crystal, there is the problem that X-rays enter even those portions which do not contribute to diffraction, deteriorating the wavelength resolution of the detected X-rays and the ratio of the intensity of the characteristic X-rays to the background intensity. In an attempt to solve this problem, Japanese Patent Laid-Open No. S52-27695 discloses a technique using a disk having various sizes of X-ray takeoff windows between a source of X-rays and an analyzing crystal. An operator can select an X-ray takeoff window matched with the effective diffraction area by manipulating the disk from outside the vacuum. However, it is not easy for the operator to select an X-ray takeoff window of appropriate size. Consequently, there is the problem that it is laborious to switch the X-ray takeoff window by manual manipulations. Furthermore, it is impossible to cope with continuous variation of X-ray wavelength.

SUMMARY OF THE INVENTION

It is an object of the present invention to provide a wavelength-dispersive X-ray spectrometer which is free of the foregoing problems. That is, only X-rays diffracted in ever optimum effective diffractive regions on the curved analyzing crystal are guided to an X-ray detector at all times without the need for the operator to make any decision.

This object is achieved in accordance with the teachings of the present invention by a wavelength-dispersive X-ray spectrometer fitted to an X-ray microarea-analyzer, such as an electron probe microanalyzer, the X-ray spectrometer being designed to collect X-rays diffracted by the curved analyzing crystal while moving the crystal straight. The X-ray spectrometer has analyzing crystals each having a crystalline lattice plane. The direction of angular dispersion of the crystalline lattice plane is so curved that it has a curvature equal to the diameter of a Rowland circle. A limitation device for limiting an incident region and/or an exit region of the surface of the curved analyzing crystal is mounted integrally with the curved analyzing crystal. Incident X-rays enter the incident region or exit from the exit region of the surface of the crystal after being diffracted and go toward an X-ray detector such that only X-rays diffracted by the effective diffractive regions of the surface of the curved analyzing crystal are detected by the X-ray detector in response to variation of the effective diffractive regions of the surface of the analyzing crystal contributing to actual diffraction when the spectral position of the X-ray spectrometer varies.

In one feature of the present invention, the limitation device is made of an X-ray blocking plate upstanding toward the inside of the Rowland circle from the position of the surface of the analyzing crystal at the end of the analyzing crystal in the direction of angular dispersion. The X-ray blocking plate blocks parts of at least one of incident X-rays going from a point source of X-rays toward the curved analyzing crystal and X-rays diffracted by the analyzing crystal toward the X-ray detector.

In another feature of the present invention, the limitation device is made of an X-ray blocking plate upstanding toward the center of the Rowland circle in the X-ray spectrometer from an end of a crystal support member that supports the analyzing crystal in the direction of angular dispersion of the crystal or toward the center of curvature of the curved analyzing crystal. The X-ray blocking plate blocks parts of at least one of incident X-rays going from a point X-ray source toward the analyzing crystal and X-rays diffracted by the analyzing crystal toward the X-ray detector.

In a further feature of the present invention, the limitation device is made of an X-ray blocking plate upstanding perpendicularly to the plane of the Rowland circle in the X-ray spectrometer and parallel to a straight line from an end of a crystal support member that supports the curved analyzing crystal in the direction of angular dispersion of the crystal. The straight line passes through the center of the curved analyzing crystal and through the center of the Rowland circle. The X-ray blocking plate blocks parts of at least one of incident X-rays going from a point X-ray source toward the analyzing crystal and X-rays diffracted by the analyzing crystal toward the X-ray detector.

In yet another feature of the present invention, the limitation device has an X-ray blocking plate disposed at an end of a crystal support member that supports the curved analyzing crystal in the direction of angular dispersion of the crystal. A part of the X-ray blocking plate provides cover over an appropriate, substantially rectangular region at an end portion of the surface of the analyzing crystal. A front-end portion of the X-ray blocking plate is made to upstand toward the center of the Rowland circle in the X-ray spectrometer or toward the center of curvature of the analyzing crystal. The upstanding portion of the X-ray blocking plate blocks parts of at least one of incident X-rays going from a point X-ray source toward the curved analyzing crystal and X-rays diffracted by the analyzing crystal toward the X-ray detector.

In an additional feature of the present invention, the limitation device has an X-ray blocking plate disposed at an end of a crystal support member that supports the curved analyzing crystal in the direction of angular dispersion of the crystal. A part of the X-ray blocking plate provides cover over an appropriate, substantially rectangular region at an end portion of the surface of the curved analyzing crystal. A front-end portion of the X-ray blocking plate is made to upstand perpendicularly to the plane of the Rowland circle in the X-ray spectrometer and parallel to a straight line passing through the center of the crystal and through the center of the Rowland circle. The upstanding portion of the X-ray blocking plate blocks parts of at least one of incident X-rays going from a point X-ray source toward the curved analyzing crystal and X-rays diffracted by the analyzing crystal toward the X-ray detector.

In one embodiment of the present invention, the analyzing crystal is a spherically-curved, Johann-type analyzing crystal. The crystal has a concave surface curved into a spherical form having the same curvature as the diameter of the Rowland circle in the direction of angular dispersion of the curved analyzing crystal and in a direction perpendicular to the angular dispersion. The shape of the portion of the X-ray blocking plate which upstands toward the inside of the Rowland circle from an end of a crystal support member that supports the spherically-curved, Johann-type analyzing crystal in the direction of angular dispersion of the crystal is substantially rectangular.

The present invention also provides a wavelength-dispersive X-ray spectrometer designed such that radiations going straight are collected, the X-ray spectrometer using curved analyzing crystals mounted therein. Each of the curved analyzing crystals has an X-ray blocking plate upstanding from the position of the surface of the analyzing crystal toward the inside of the Rowland circle. The height of the X-ray blocking plate is so determined that a region thereof contributing to diffraction is set based on data indicating error in incident angle of X-rays incident on the surface of the curved analyzing crystal.

In yet an additional feature of the present invention, the curved analyzing crystal is an analyzing element made of a layered synthetic microstructure having a lattice spacing of less than 2 nm. The limitation device is formed integrally with the analyzing element made of layered synthetic microstructure.

According to the present invention, when an analysis is made using a curved analyzing crystal which is mounted in a wavelength-dispersive X-ray spectrometer designed to collect X-rays diffracted by the curved analyzing crystal while moving the crystal straight, a limitation device is mounted integrally with the curved analyzing crystal. The direction of angular dispersion of the crystalline lattice plane of the analyzing crystal has a curvature equal to the diameter of the Rowland circle. The surface of the curved analyzing crystal has an effective diffractive region contributing to actual diffraction. As the spectral position of the X-ray spectrometer varies, the effective diffractive region varies. Correspondingly, the limitation device limits at least one of the incident regions of the surface of the curved analyzing crystal from which incident X-rays enter and the exit region of the surface of the analyzing crystal from which X-rays are diffracted toward the X-ray detector such that only X-rays diffracted by the effective diffractive region of the surface of the analyzing crystal are detected by the X-ray detector. Consequently, only the X-rays diffracted by the effective diffractive region of the surface of the curved analyzing crystal can be guided to the X-ray detector at all times for every wavelength of X-rays within the spectral range without the need for the operator to make any decision or perform any manipulation. As a result, X-rays on portions not contributing to diffraction can be prevented; otherwise, abnormal waveforms would be produced and the spectrally selective performance would be deteriorated. Hence, the wavelength resolution of characteristic X-rays used for analysis and the ratio of the intensity of the characteristic X-rays to the background intensity can be improved.

Other objects and features of the invention will appear in the course of the description thereof, which follows.

BRIEF DESCRIPTION OF THE DRAWINGS

FIG. 1 is a diagram illustrating the fundamental structure of a wavelength-dispersive X-ray spectrometer of a straight moving ray-collection type, the spectrometer being equipped with curved analyzing crystals;

FIG. 2 is a diagram illustrating incident angle error $\Delta\theta$ on an analyzing crystal under the Bragg condition, and in which the analyzing crystal consists of a spherically-curved Johann crystal;

FIGS. 8(a) and 8(b) illustrate the principle of a Johann analyzing crystal;

FIGS. 12(a), 12(b), 12(c), and 12(d) show examples of characteristic X-ray spectra acquired using a curved analyzing element of a layered synthetic microstructure, using no X-ray blocking plates; and FIGS. 13(a), 13(b), 13(c), and 13(d) show examples of characteristic X-ray spectra acquired using a curved analyzing element of a layered synthetic microstructure, using X-ray blocking plates.

DESCRIPTION OF THE PREFERRED EMBODIMENTS

Figures 3A, 3B:
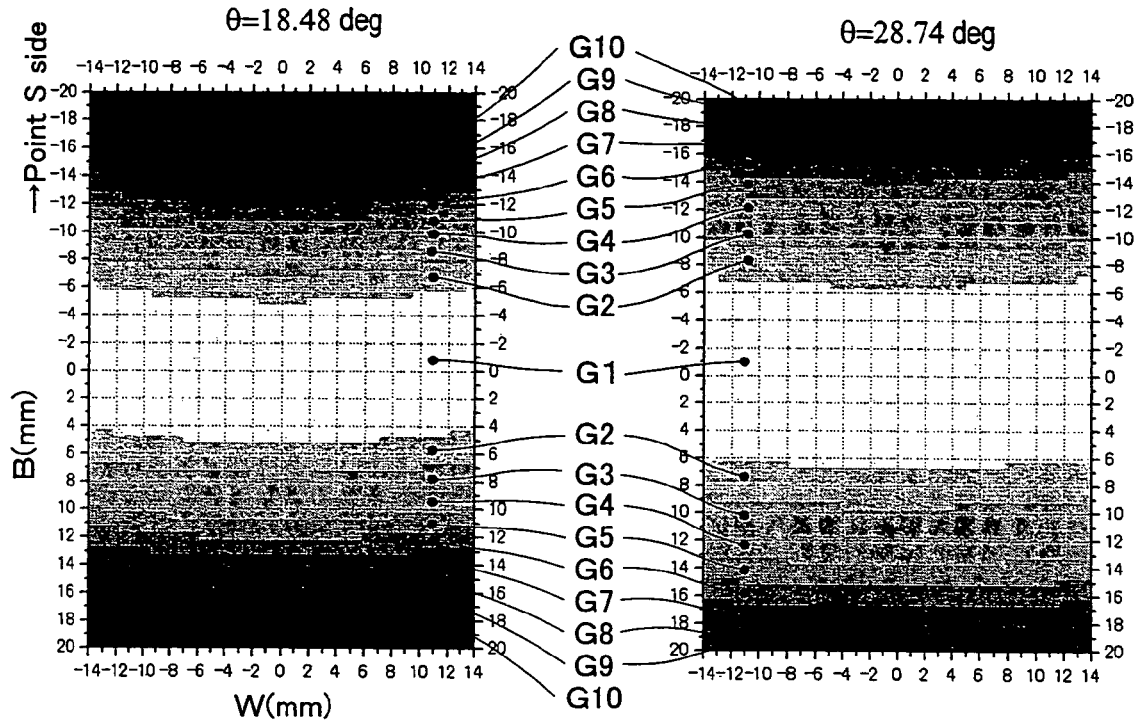
FIGS. 3(a), 3(b), 3(c) and 3(d) are diagrams showing examples of computation of incident angle error $\Delta\theta$ on the surface of a spherically-curved Johann crystal fitted to a wavelength-dispersive X-ray spectrometer having a Rowland circle with a radius of 140 mm, the spectrometer of a straight moving ray-collection type.
Figures 3C, 3D:
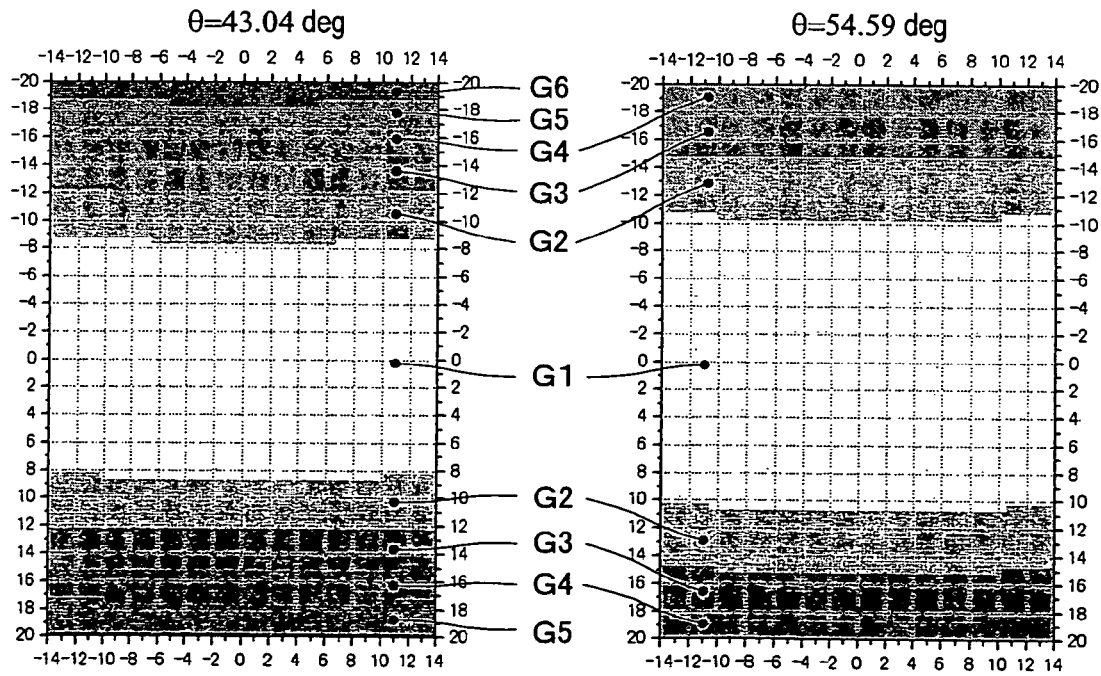

Embodiments of the present invention are hereinafter described with reference to the accompanying drawings. It is to be understood that the scope of the present invention is not limited thereto. Components operating identically or similarly are indicated by the same reference numerals in various figures and their repeated description will be avoided.

When a spherically-curved Johann analyzing crystal is used as a curved analyzing crystal, effective diffractive regions should be discussed. The effective diffractive regions are first described. FIG. 2 illustrates incident angle error $\Delta\theta$ on a spherically-curved Johann analyzing crystal under a Bragg condition given by Eq. (2). Incident angle error $\Delta\theta$ at an arbitrary point P on the crystal is given by $$\Delta\theta = \theta_p - \theta \quad (4)$$

where $\theta$ is the incident angle of X-rays to the center C of the analyzing crystal and $\theta_p$ is the incident angle of X-rays on the point P. FIGS. 3(a)-3(d) show examples of calculation of incident angle error $\Delta\theta$ on the surface of the spherically-curved Johann analyzing crystal fitted to a wavelength-dispersive X-ray spectrometer of the straight moving ray-collection type having a Rowland circle with a radius of 140 mm. The values of incident angle error $\Delta\theta$ obtained when the incident angle $\theta$ is 18.48°, 28.74°, 43.04°, and 54.59°, respectively, are shown in FIGS. 3(a), 3(b), 3(c), and 3(d), respectively. Regions G1-G10 are indicated by different degrees of concentration and denote various magnitudes of incident angle error $\Delta\theta$. The regions G1-G10 have relationship shown in Table 1, where K=0.0005 radian.

TABLE 1

| region | corresponding incident angle error $\Delta\theta$ |
| --- | --- |
| G1 | $-K < \Delta\theta < K$ |
| G2 | $K \leq \Delta\theta < 2K$ |
| G3 | $2K \leq \Delta\theta < 3K$ |
| G4 | $3K \leq \Delta\theta < 4K$ |
| G5 | $4K \leq \Delta\theta < 5K$ |
| G6 | $5K \leq \Delta\theta < 6K$ |
| G7 | $6K \leq \Delta\theta < 7K$ |
| G8 | $7K \leq \Delta\theta < 8K$ |

TABLE 1-continued

| region | corresponding incident angle error $\Delta\theta$ |
| --- | --- |
| G9 | $8K \leq \Delta\theta < 9K$ |
| G10 | $9K \leq \Delta\theta$ |

It can be considered that in a normal effective diffractive region of the Johann analyzing crystal, incident angle error $\Delta\theta$ is in the range of about ±3 to 4 K. As can be seen from FIGS. 3(a)-3(d), the incident angle error $\Delta\theta$ on the surface of the spherically-curved Johann analyzing crystal fitted to the WD spectrometer of the straight moving ray-collection type increases with going away from the center position in the direction of angular dispersion. Furthermore, it can be seen that the magnitude of the incident angle error $\Delta\theta$ depends on the incident angle $\theta$ and increases with reducing the incident angle $\theta$ and vice versa. On the other hand, at positions moved away from the widthwise center vertically to the Rowland circle in the X-ray spectrometer, the magnitude of the incident angle error $\Delta\theta$ is substantially the same as the magnitude at the widthwise center. Accordingly, the effective diffractive region on the surface of the spherically-curved Johann analyzing crystal fitted to the WD spectrometer of the straight moving ray-collection type is determined by the length in the direction of angular dispersion. This length depends on the incident angle $\theta$. It can be seen that the length increases with increasing the incident angle $\theta$ and vice versa.

Based on the above-described findings, a spherically-curved, Johann-type analyzing crystal fitted to a WD spectrometer of the straight moving ray-collection type is so fabricated that it has an optimum length in the direction of angular dispersion for X-rays close to the longest wavelength limit (i.e., maximum value of incident angle $\theta$) within the spectral range determined by the fitted WD spectrometer. When shorter wavelengths of X-rays within the spectrometer spectral range are spectrally diffracted, if the effective diffractive region in the direction of angular dispersion is limited according to the spectral position L without limiting the widthwise length of the analyzing crystal, only X-rays diffracted by the effective diffractive region of the surface of the analyzing crystal are detected by the X-ray detector for every wavelength of X-rays within the spectral range; otherwise, the spectral resolving performance would be deteriorated. Consequently, the wavelength resolution of the characteristic X-rays used for analysis and the ratio of the intensity of characteristic X-rays to the intensity of background can be improved.

In the present invention, as a method of limiting the effective diffractive region of an analyzing crystal in the direction of angular dispersion according to the spectral position L, an X-ray blocking plate is mounted near each end of the curved analyzing crystal in the direction of angular dispersion. The blocking plate is made to upstand from the position of the surface of the crystal toward the inside of a Rowland circle. The X-ray blocking plate blocks parts of at least one of incident X-rays going from a point X-ray source toward the analyzing crystal and X-rays diffracted by the analyzing crystal toward the X-ray detector. However, the thickness and mechanical strength of the analyzing crystal are not sufficient. Therefore, it is difficult to mount the X-ray blocking plate directly to the analyzing crystal. Consequently, in practice, the X-ray blocking plate is mounted to a crystal support member that supports the analyzing crystal. At this time, it is only necessary that the only portions of the blocking plates that upstand from the position of the surface of the crystal are located close to the ends of the crystal in the direction of angular dispersion. Furthermore, the crystal support member to which the X-ray blocking plate is mounted is not limited to a member to which the analyzing crystal can be directly mounted. Any member can be used which is located close to the end of the analyzing crystal in the direction of angular dispersion and which has a mechanical positional relationship with the analyzing crystal, the positional relationship not being varied if the incident angle θ is varied, i.e., the member moving together with the analyzing crystal. A method of mounting the X-ray blocking plate to the crystal support member consists of using adhesive or fixing the blocking plate with small screws.

Figure 4A:
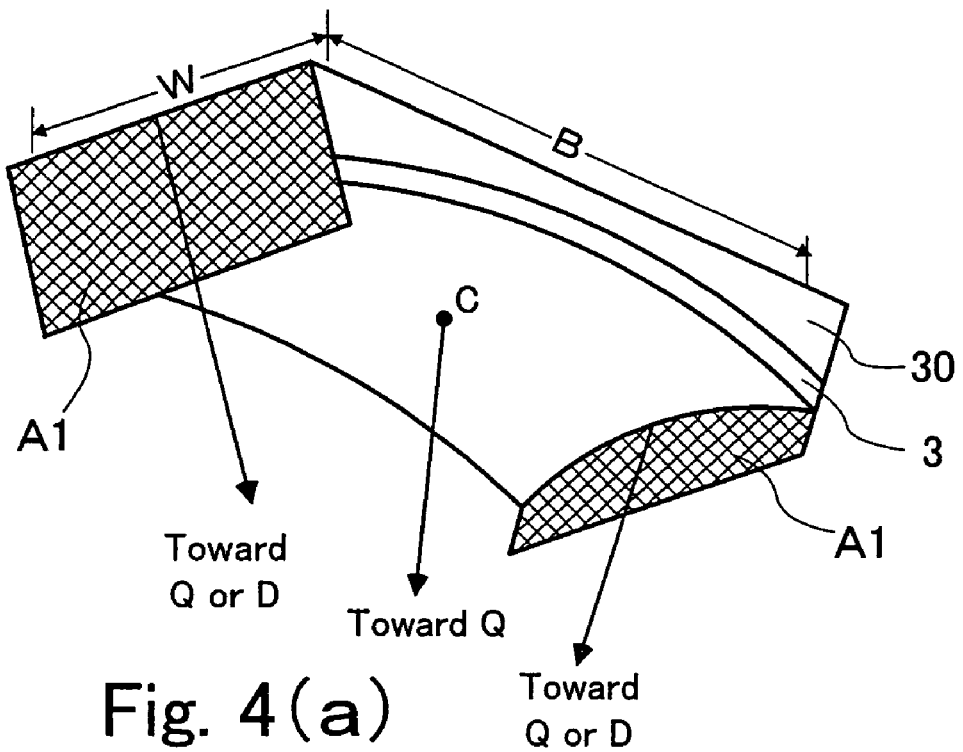
FIGS. 4(a) and 4(b) show an X-ray blocking plate mounted to an end of a crystal support member 30, and in which the blocking plate has been made to upstand toward the inside of a Rowland circle.
Figure 4B:
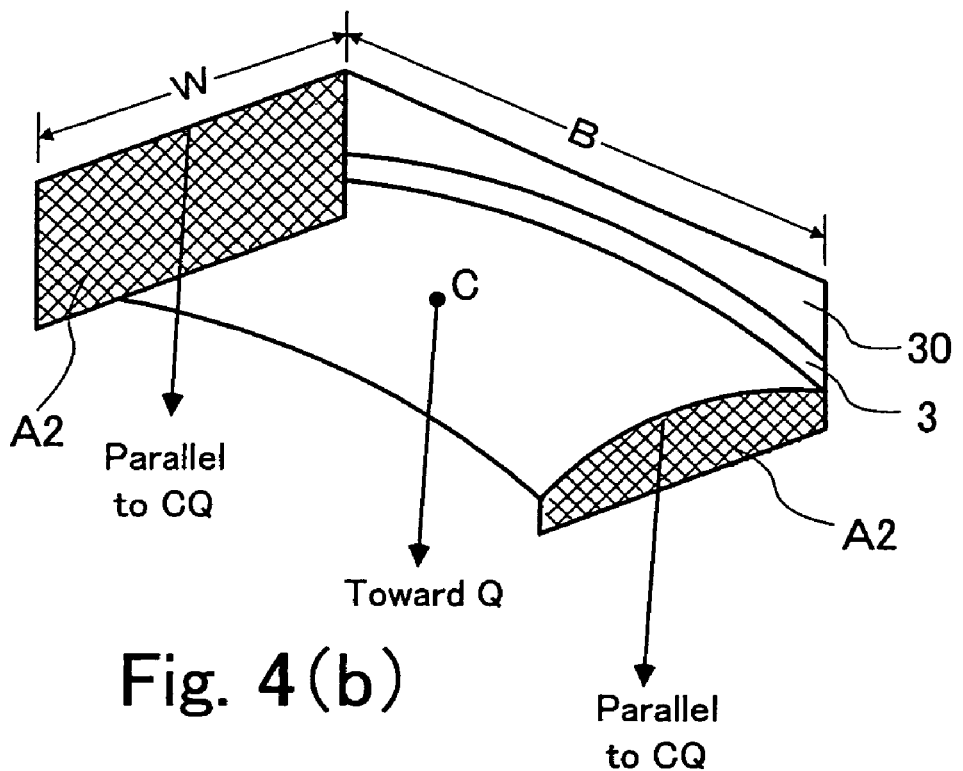

FIGS. 4(a) and 4(b) show examples of X-ray blocking plates, each of which is made to upstand directly from an end of a crystal support member in the direction of angular dispersion of a curved angular crystal. If the X-ray blocking plate upstanding toward the inside of a Rowland circle is directed toward the center Q of the Rowland circle in the spectrometer or toward a point D as shown in FIG. 4(a), or if the blocking plate is made perpendicularly to the plane of the Rowland circle in the X-ray spectrometer and parallel to a straight line which passes through the center C of the analyzing crystal and the center Q of the Rowland circle as shown in FIG. 4(b), it is easy to find the necessary height by geometrical computations as described later.

Figure 5A:
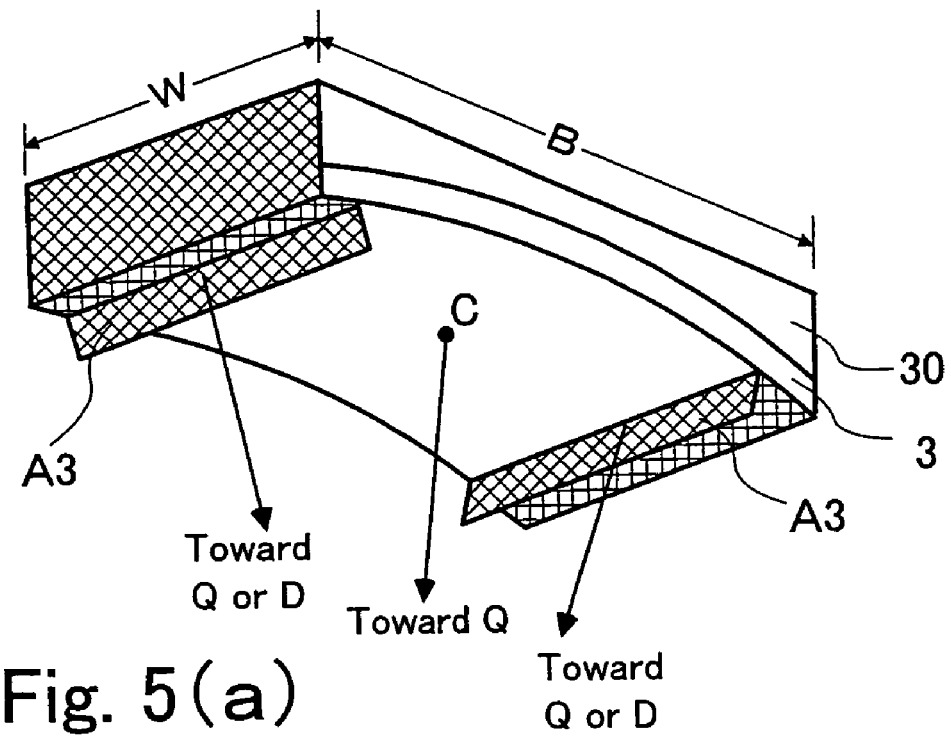
FIGS. 5(a) and 5(b) show an X-ray blocking plate mounted to an end of a crystal support member, and in which a part of the plate has been bent, an appropriate substantially rectangular region of an end portion of the surface of a curved analyzing crystal is covered, and a front-end portion of the plate is made to upstand toward the inside of the Rowland circle.
Figure 5B:
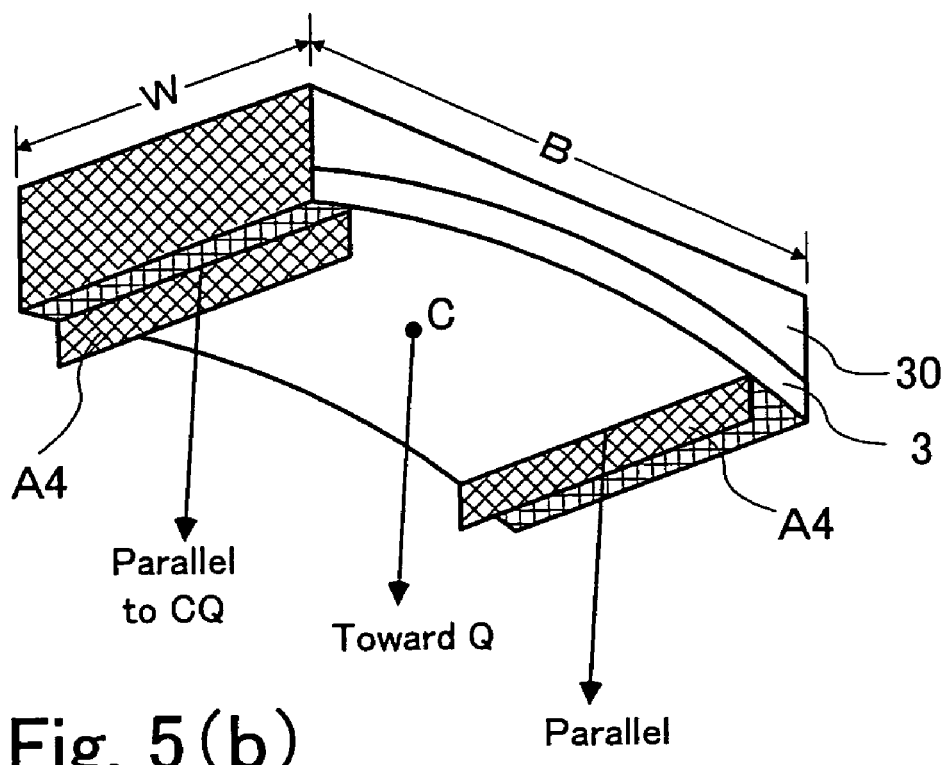

During the process where an analyzing crystal in the form of a flat plate is curved or further bent into a spherical form, end portions of the crystal tend to be curved non-uniformly. If so, X-rays are not correctly diffracted in these regions. This leads to a deterioration of the performance. Therefore, a part of the X-ray blocking plate may first cover a substantially rectangular appropriate region of an end portion of the surface of the curved analyzing crystal and then a front-end portion of the X-ray blocking plate may be made to upstand toward the inside of a Rowland circle in the X-ray spectrometer as shown in FIGS. 5(a) and 5(b) without causing the X-ray blocking plate to upstand directly from an end of the crystal support member in the direction of angular dispersion of the analyzing crystal. Also, in this case, it is easy to calculate the height if the X-ray blocking plate upstanding toward the inside of the Rowland circle is directed toward the center Q of the Rowland circle in the spectrometer or point D as shown in FIG. 5(a) or if the plate is made perpendicularly to the plane of the Rowland circle in the X-ray spectrometer and parallel to a straight line passing through the center C of the analyzing crystal and through the center Q of the Rowland circle as shown in FIG. 5(b).

Figure 6:
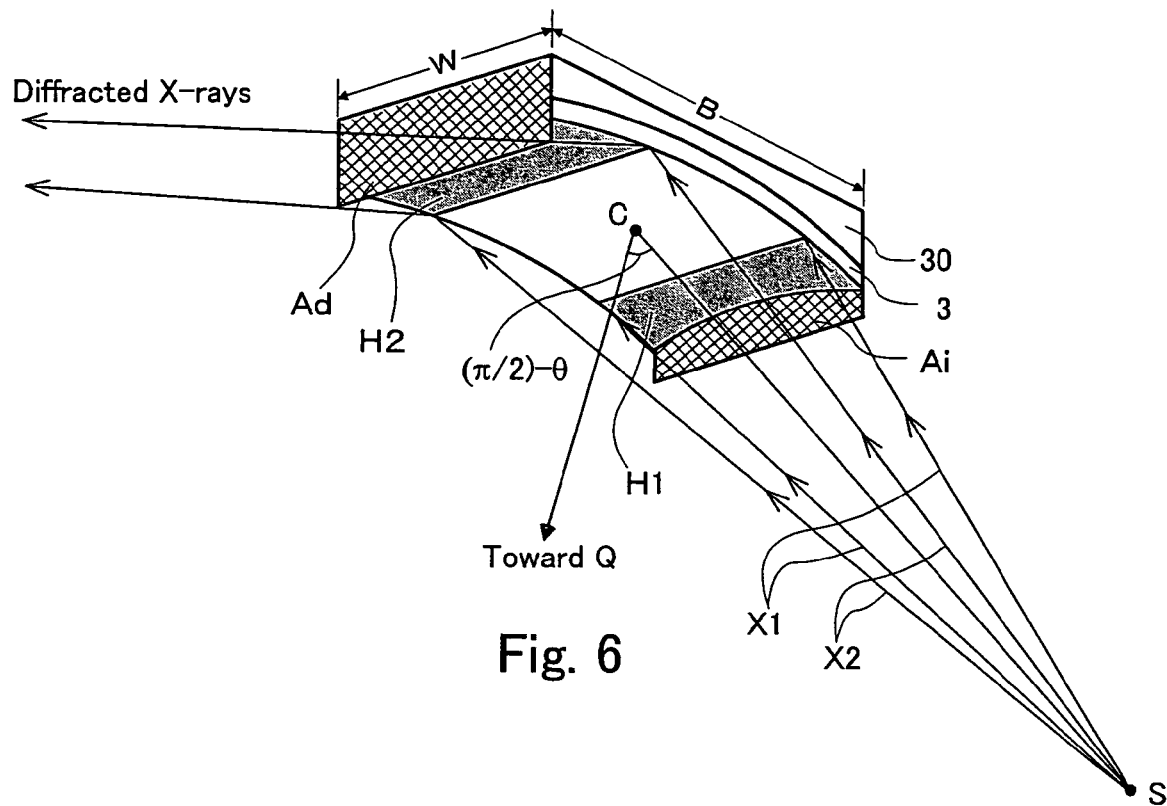
FIG. 6 shows an example of X-ray blocking plate made to upstand perpendicularly to the plane of the Rowland circle in the X-ray spectrometer and parallel to a straight line which passes through the center of an analyzing crystal and the center of a Rowland circle, illustrating that the X-ray blocking plate blocks parts of at least one of incident X-rays going from a point X-ray source toward the analyzing crystal and X-rays diffracted by the analyzing crystal toward the X-ray detector.
Figure 9:
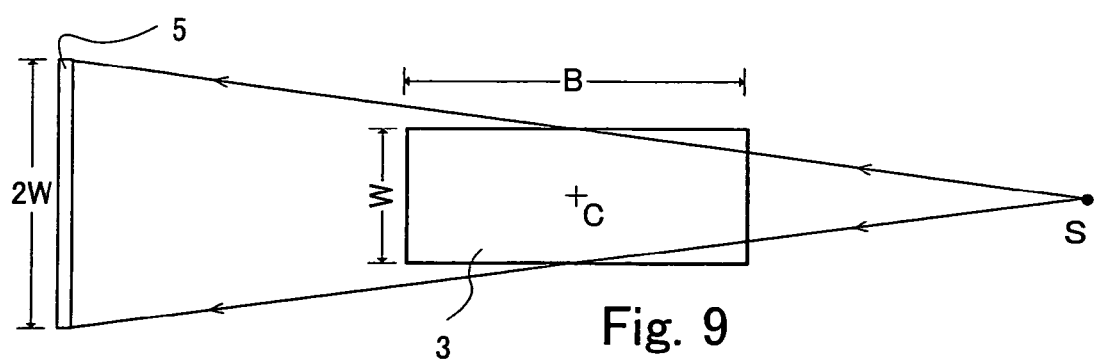
FIG. 9 is a diagram illustrating the relationship between the width of a curved analyzing crystal and the length of a slit in an X-ray detector.
Figure 7A:
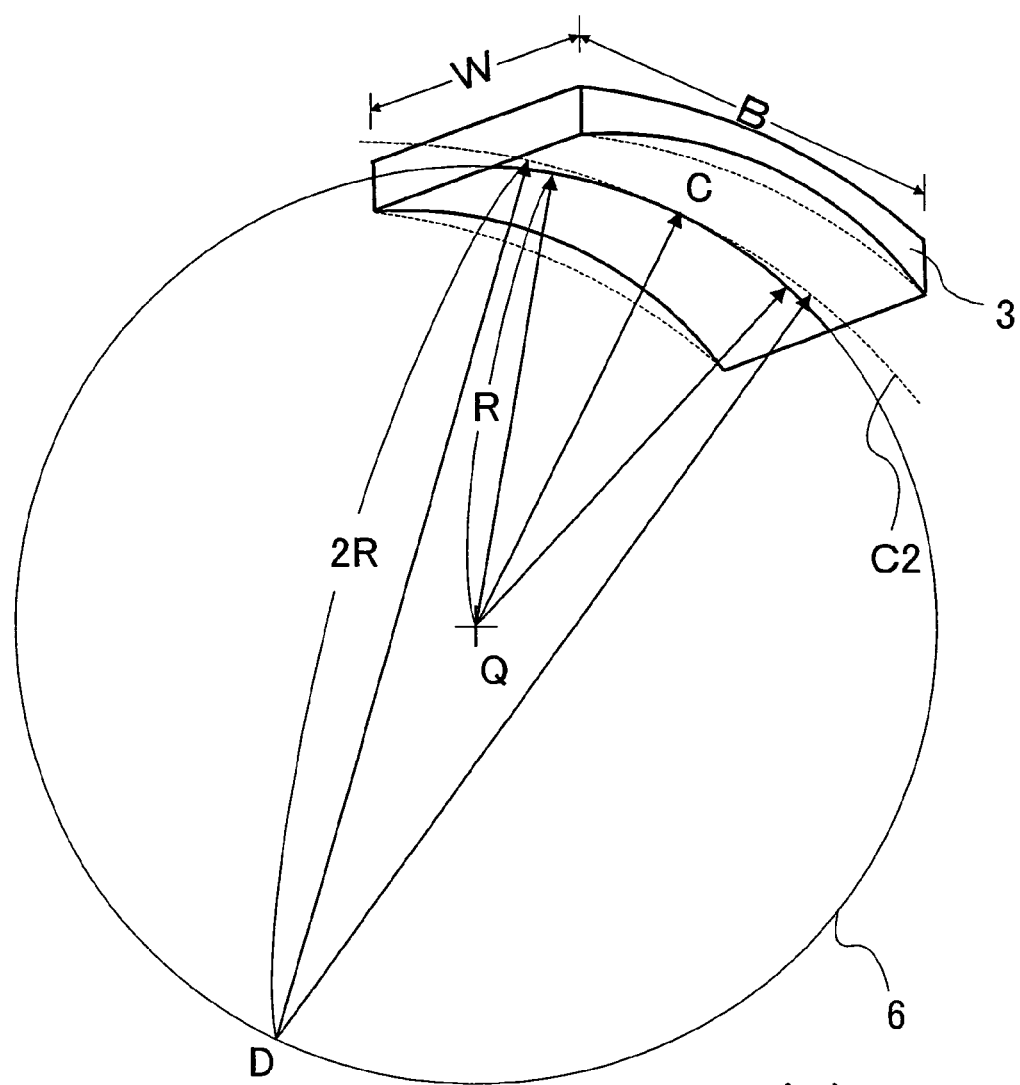
FIGS. 7(a) and 7(b) illustrate the principle of a Johansson analyzing crystal.
Figure 7B:
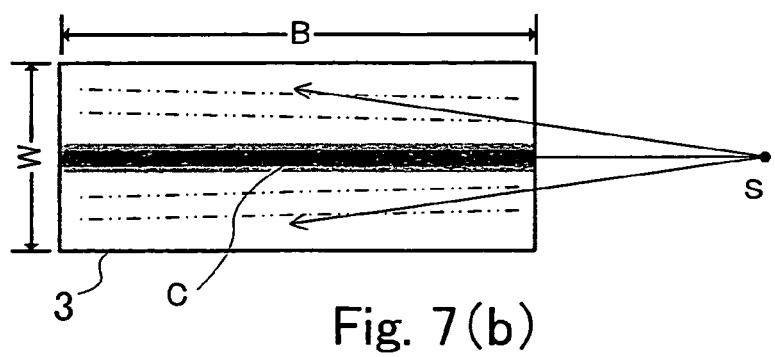

FIG. 6 illustrates the manner in which non-contributing regions H1 and H2 are created by X-ray blocking plates, each of which is made to upstand perpendicularly to the plane of the Rowland circle in the X-ray spectrometer and parallel to a straight line passing through the center C of an analyzing crystal and the center Q of a Rowland circle in the case of FIG. 4(b). Of incident X-rays X1 emitted from a point X-ray source S toward an analyzing crystal 3, X-ray components going toward the non-contributing region H1 on the crystal near side of the point X-ray source S are blocked by an X-ray blocking plate Ai from reaching the surface of the crystal. Of incident X-rays X2, X-ray components hitting the non-contributing region H2 on the crystal farther side of the point X-ray source S are diffracted by the surface of the crystal but blocked by an X-ray blocking plate Ad from reaching the X-ray detector. That is, the region which is located between the non-contributing regions H1 and H2 and which permits the incident X-rays to hit the crystal surface and the exiting diffracted X-rays to reach the X-ray detector contributes to diffraction.

Figure 10:
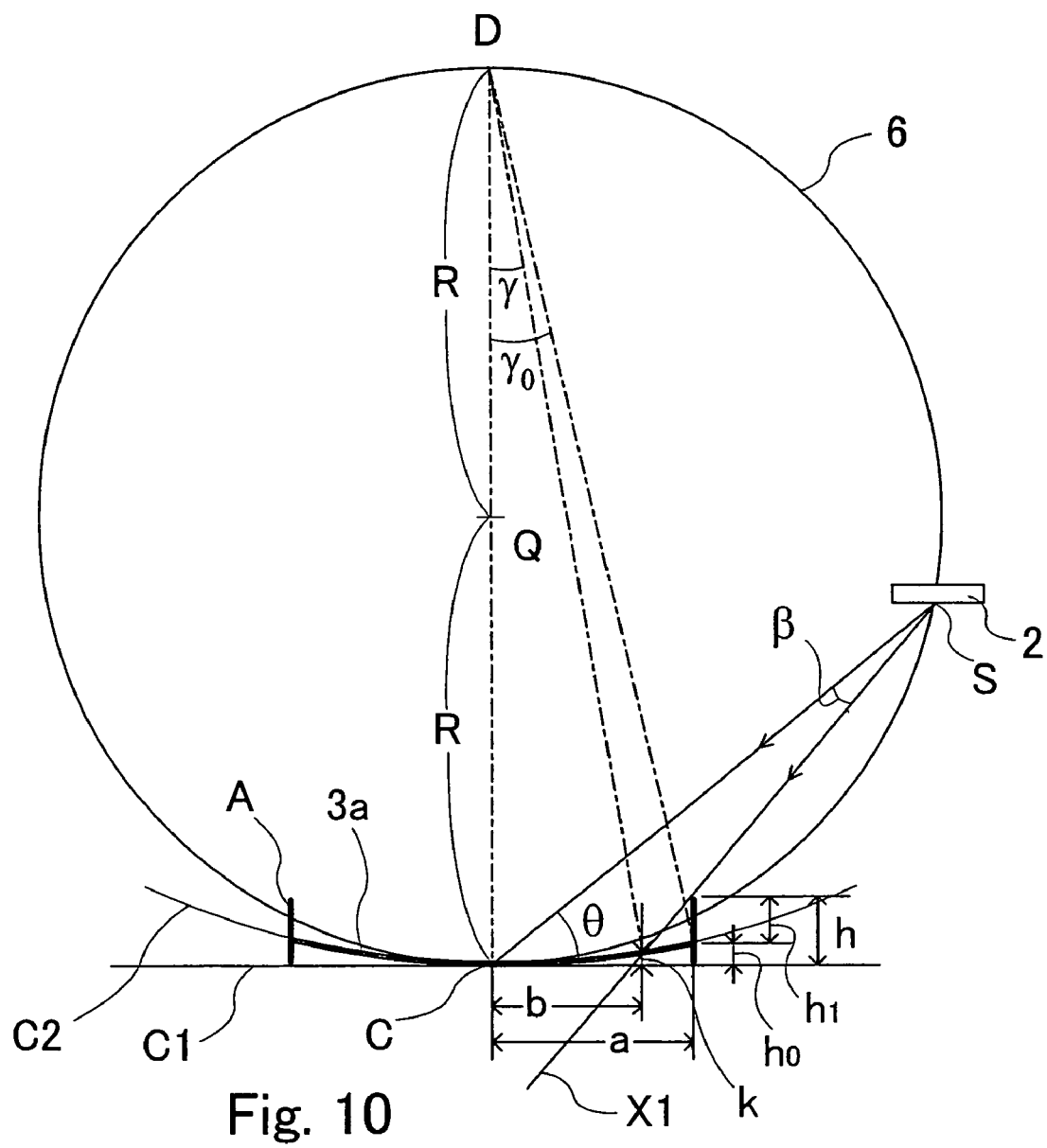
FIG. 10 is a diagram illustrating a method of calculating the height of an X-ray blocking plate when it is made to upstand perpendicularly to the plane of the Rowland circle in the X-ray spectrometer and parallel to a straight line passing through the center of an analyzing crystal and through the center of a Rowland circle.

Appropriate height of the X-ray blocking plates that are made to upstand from the position of the surface of the curved analyzing crystal is determined by the size of the Rowland circle in the X-ray spectrometer and the length of the crystal in the direction of angular dispersion. A method of calculating the height of an X-ray blocking plate is described by taking the case in which the X-ray blocking plate is made to upstand perpendicularly to the plane of the Rowland circle in the X-ray spectrometer and parallel to a straight line passing through the center C of the analyzing crystal and the center Q of the Rowland circle as an example by referring to FIG. 10. For the sake of convenience, the center C of the analyzing crystal is taken as the origin of coordinates in FIG. 10. Since the input side and output side of the crystal are symmetrical, only the input side is shown. The surface $3a$ of the crystal is on an arc C2 of curvature 2R.

Let a be the horizontal distance from the center C of the analyzing crystal to the X-ray blocking plate. Let h be the height of the X-ray blocking plates from the height of the center C of the analyzing crystal in a direction parallel to the direction directed toward the center Q of the Rowland circle. Let $h_0$ be the height from the height of the center C of the crystal to the position of the crystal surface in the longitudinal end of the crystal. Let $h_1$ be the height from the position of the crystal surface in the longitudinal end of the crystal to the front end of the X-ray blocking plate. Let b be the horizontal distance from the center C of the analyzing crystal to the front end of the shadow created by the X-ray blocking plate (intersection of the crystal surface $3a$ and X1). Let k be the height from the height of the center C of the analyzing crystal to the intersection of the crystal surface $3a$ and X1. Let R be the radius of the Rowland circle. Let θ be the incident angle. Angles $\gamma_0$ and $\gamma$ shown in the figure are given by $$\gamma_0 = \arctan \frac{a}{2R} \quad (5)$$

$$\gamma = \arcsin \frac{b}{2R} \quad (6)$$

Therefore, from Eqs. (5) and (6), the heights k and $h_0$ are given by $$k = 2R \cdot (1 - \cos\gamma) \quad (7)$$

$$h_0 = 2R \cdot (1 - \cos\gamma_0) \quad (8)$$

An angle β is given by $$\beta = \arctan \frac{\cos(\theta - \gamma) - \cos\theta}{\sin(\theta - \gamma)} \quad (9)$$

Alternatively, the angle β is approximately given by $$\beta \cong \frac{\gamma \cdot \sin\theta}{\sin\theta - \gamma \cdot \cos\theta} \quad (10)$$

Therefore, using k in Eq. (7) and β in Eq. (9) or (10), the height h is given by $$h = (a-b) \cdot \tan(\theta+\beta) + k \quad (11)$$

From Eqs. (8) and (11), the height $h_1$ is found from the equation:

$$h_1 = h - h_0 \quad (12)$$

Although the height of the X-ray blocking plate can be found similarly in the case of FIGS. 4(a) and 5(a), its detailed description is omitted.

Specific Embodiment

An example in which the height of the X-ray blocking plate was found under the conditions where R=140 mm and α=20 mm by the aforementioned method is described below. b is the distance on the side of the X-ray generation point S in the direction of angular dispersion under the actual conditions where the incident angle error Δθ enables regions G1-G3 and where region G4 and the following regions are shielded by the X-ray blocking plate. The results of calculation are shown in Table 2.

TABLE 2

| | incident angle θ (in degrees) | | | | |
|---|---|---|---|---|---|
| | 18.48 | 28.74 | 43.04 | 54.59 | average |
| b (mm) | 8.3 | 10.8 | 14.3 | 17.9 | — |
| h (mm) | 4.4 | 5.7 | 6.3 | 4.0 | 5.1 |
| $h_1$ (mm) | 3.7 | 5.0 | 5.6 | 3.3 | 4.4 |

As shown in Table 2, the required height of the X-ray blocking plate can be determined from data obtained by calculating the incident angle error Δθ. Meanwhile, the results shown in Table 2 indicate that if the height h of the X-ray blocking plate or $h_1$ is determined such that effective diffractive regions having similar levels of incident angle error Δθ are set, the value of the height h varies depending on the incident angle θ and is not always kept constant. Although this tendency somewhat varies depending on the size of the Rowland circle, on the length of the analyzing crystal in the direction of angular dispersion, and on the direction in which the X-ray blocking plate is made to upstand, the value of the height h generally tends to increase when the incident angle θ is relatively close to the midpoint of the spectral range as shown in Table 2. Accordingly, if the average value of the values of the height h corresponding to different values of the incident angle θ is taken as the height of the X-ray blocking plate, an optimum or nearly optimum average effective diffractive region can be set over the whole spectral range. Alternatively, if an element that is most important or used most frequently within the spectral range, the height h may be set according to the incident angle θ of the characteristic X-rays of that element. Where limitations are imposed on the mechanism of the X-ray spectrometer, it is not always necessary that an X-ray blocking plate be mounted at each of the opposite ends of the analyzing crystal. An X-ray blocking plate may be mounted at any one end.

Furthermore, as can be seen from FIGS. 3(a)-3(d), the spread of the region in which the magnitude of the incident angle error Δθ is constant is not symmetrical in the direction of angular dispersion with respect to the center C of the analyzing crystal. The spread is somewhat narrower on the side of the point X-ray source S of X-rays. Therefore, the height h found from the value of the horizontal distance b on the side of the point X-ray source S, the value of b on the opposite side or the average value may be taken as the height of the X-ray blocking plate at each end. The height on the side of the point X-ray source S of X-rays and the height on the opposite side may be set to different appropriate values.

Figure 11A:
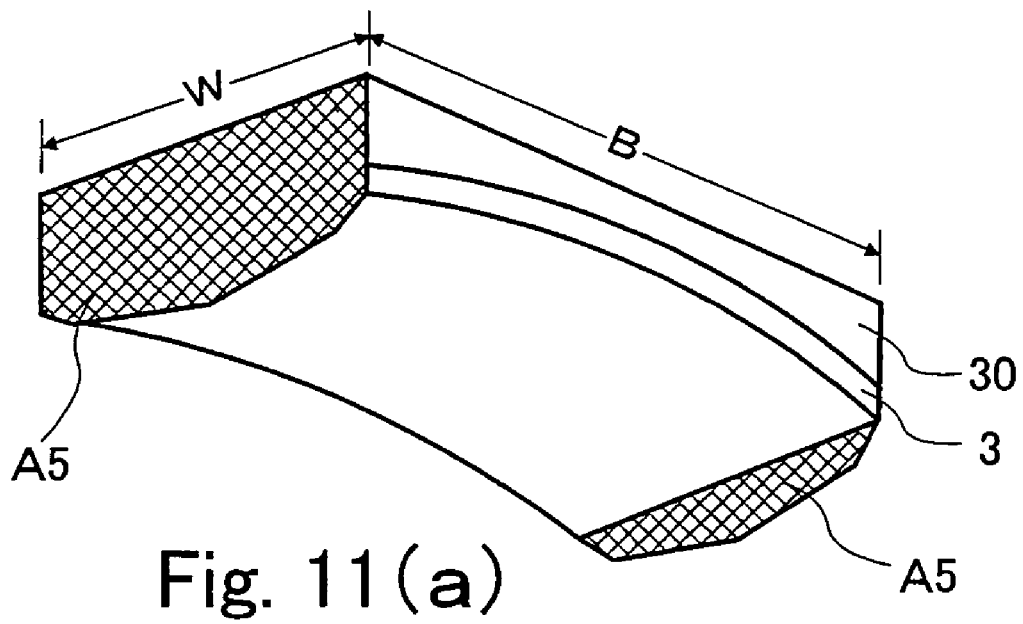
FIGS. 11(a) and 11(b) show examples of X-ray blocking plates having non-rectangular shapes.
Figure 11B:
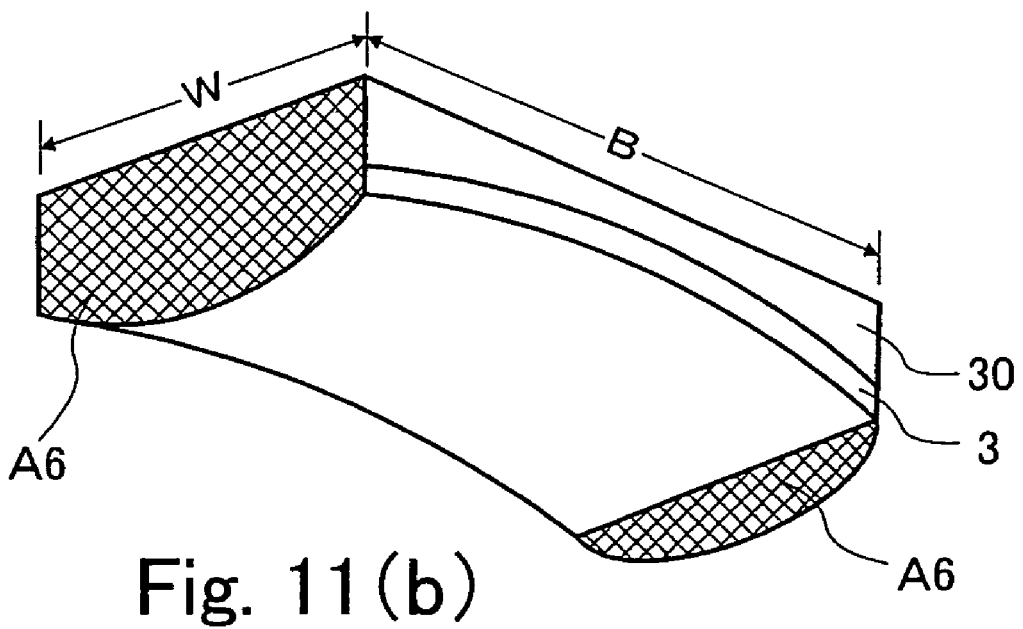

In the description of the embodiments of the present invention provided so far, a spherically-curved, Johann-type analyzing crystal is taken as an example. As shown in FIGS. 3(a)-3(d), the region of the spherically-curved, Johann-type analyzing crystal to be blocked is substantially rectangular. Therefore, as shown in FIGS. 4(a) and 4(b) and FIGS. 5(a) and 5(b), the shape of the X-ray blocking plate that is made to upstand may be substantially rectangular. However, in the case of an ordinary analyzing crystal in a Johann geometry curved only in the direction of angular dispersion, the shape of the region in which the incident angle error Δθ increases as shown in FIG. 8(b) does not assume a simple rectangular form. Even in this case, the fully diffractive region while completely satisfying Eq. (2) like the letter X expands and contracts in the direction of angular dispersion according to the value of the incident angle θ (the letter X expands in the direction of angular dispersion according to increasing the value of θ) and so certain advantages can be obtained even if the shape of the X-ray blocking plate made to upstand is substantially rectangular. In addition, if the X-ray blocking plate is shaped like a triangle or an arc directed toward the front end, such as X-ray blocking plates A5 and A6 as shown in FIGS. 11(a) and 11(b), it is obvious that the regions not contributing to diffraction can be more effectively shielded at least in the direction of angular dispersion.

The present invention is implemented in an analyzing element made of a layered synthetic microstructure in the manner described below. Where a layered synthetic microstructure is used, an analyzing element adapted for the purpose of use can be fabricated by appropriately selecting a combination of materials used for the stacked layers and the spacing between the stacked layers (i.e., the lattice spacing). One typical example of layered synthetic microstructure analyzing element that has been put into practical use is an element using layers of tungsten and silicon at a lattice spacing of about 3 nm. Another example is an element using layers of nickel and carbon at a lattice spacing of about 5 nm. A further example is an element using layers of molybdenum and carbon tetraboride at a lattice spacing of about 10 nm.

In recent years, with improvement of the technique for fabricating layered synthetic microstructure, attempts have been made to fabricate layered synthetic microstructure having smaller lattice spacing than heretofore. FIGS. 12(a)-12(d) show characteristic X-ray spectra derived by an analyzing element mounted to a wavelength-dispersive X-ray spectrometer of the straight moving ray-collection type without using any X-ray blocking plate. The analyzing element has a layered synthetic microstructure having a lattice spacing of about 1.5 nm, which has a curvature equal to the diameter of the Rowland circle in the direction of angular dispersion. In the graphs of FIGS. 12(a)-(d), X-ray intensity is plotted on the vertical axis on an arbitrary scale. The spectral position L when the radius of the Rowland circle is 140 mm is plotted on the horizontal axis. The position L is given by Eq. (3) and represented in millimeters. Spectra of FIGS. 12(a)-12(d) are close to Si—Kα (wavelength of 0.713 nm), Al—Kα (wavelength of 0.834 nm), Mg—Kα (wavelength of 0.989 nm), and F—Kα (wavelength of 1.832 nm), respectively. In this analyzing element of layered synthetic microstructure, the incident angle θ when each characteristic X-ray is diffracted is about 13.7° for Si—Kα, about 16.1° for Al—Kα, about 19.2° for Mg—Kα, and about 37.6° for F—Kα. In each spectrum, the left side on the paper indicates the lower angle side having smaller incident angle θ (the same as the shorter wavelength side).

In the spectrum of FIG. 12(a), an abnormal bumpy hill appears clearly on the lower angle side of Si—Kα. In the spectrum FIG. 12(b), an abnormal bumpy hill appears slightly and an abnormally long tail appears on the lower angle side of Al—Kα. In the spectrum of FIG. 12(c), no abnormal bumpy hill is observed but the lower angle side of Mg—Kα has an abnormally long tail. The spectrum of FIG. 12(d) in which only satellite lines of F—Kα are observed is normal. That is, it can be seen that the waveform becomes more abnormal with reducing the incident angle θ of X-rays.

Spectra of FIGS. 13(a)-13(d) are close to Si—Kα, Al—Kα, Mg—Kα, and F—Kα, respectively, and have been obtained by using the analyzing element of layered synthetic microstructure from which the spectra of FIGS. 12(a)-12(d) have been taken. The X-ray blocking plate shown in FIG. 11(a) was attached to the analyzing elements. In each spectrum, Kβ-line or satellite line(s) are observed other than Kβ-line. An abnormal bump or tailing on the lower angle side is not observed unlike in the spectra of FIGS. 12(a)-12(d). The results indicate that when X-rays enter at a small incident angle θ, a normal waveform is obtained by the action of the X-ray blocking plate.

We conducted similar experiments on curved analyzing elements made of layered synthetic microstructure having lattice spacing of about 2 nm and about 3 nm, respectively. We have confirmed that in the case of the curved analyzing element of the layered synthetic microstructure having a lattice spacing of about 2 nm, the X-ray blocking plate works effectively. However, in the case of the curved analyzing element of the layered synthetic microstructure having a lattice spacing of about 3 nm, the full width at half maximum (FWHM) of the F—Kα line decreases only by several percent even if a large X-ray blocking plate that reduces the intensity of F—Kα line to about 60 to 70% is mounted. Consequently, an X-ray blocking plate is not necessary. Accordingly, our experiment reveals that in the case of a curved analyzing element of a layered synthetic microstructure fitted to an X-ray spectrometer of the straight moving ray-collection type, if the lattice spacing of the analyzing element is less than 2 nm, the X-ray blocking plate for using only an effective diffractive region of the analyzing element removes abnormal waveform portions and thus works effectively to produce a normal waveform. In other words, in cases where an X-ray analysis is performed using an analyzing element of layered synthetic microstructure having a lattice spacing of less than 2 nm, the X-ray blocking plate mentioned above is necessary to carry out the analysis reliably.

A layered synthetic microstructure analyzing element producing the spectra shown in FIGS. 12(a)-12(d) and FIGS. 13(a)-13(d) is fabricated by stacking multiple synthetic layers of film on the surface of a flat substrate, and curving the film into a Johann geometry. One method of fabricating an analyzing element with a layered synthetic microstructure consists of shaping the substrate itself into a curved geometry, such as Johann geometry or spherically-curved Johann geometry, and then stacking multiple synthetic layers of film on the substrate. With respect to an analyzing element having a layered synthetic microstructure formed on a previously curved surface, abnormal waveforms can be removed using an X-ray blocking plate in the same way as in the foregoing embodiment and a normal waveform can be obtained.

Having thus described my invention with the detail and particularity required by the Patent Laws, what is desired protected by Letters Patent is set forth in the following claims.

The invention claimed is:

1. A wavelength-dispersive X-ray spectrometer of a straight moving ray-collection type, the spectrometer being fitted to an X-ray microarea-analyzer such as an electron probe microanalyzer, said X-ray spectrometer comprising:
a curved analyzing crystal having a crystalline lattice plane curved to have a curvature equal to the diameter of a Rowland circle in a direction of angular dispersion; and
limitation means mounted integrally with the curved analyzing crystal, the limitation means acting to limit at least one of an incident region of a surface of the analyzing crystal on which incident X-rays impinge and an exit region of the surface of the analyzing crystal from which diffracted X-rays exit toward an X-ray detector such that only X-rays diffracted by an effective diffractive region of the surface of the analyzing crystal are detected by the X-ray detector in response to variation of the effective diffractive region of the surface of the analyzing crystal contributing to actual diffraction when a spectral analysis position of the X-ray spectrometer varies.

2. A wavelength-dispersive X-ray spectrometer of a straight moving ray-collection type as set forth in claim 1, wherein said limitation means is made of an X-ray blocking plate made to upstand from a position on the surface of the analyzing crystal at an end in the direction of angular dispersion of the crystal toward inside of the Rowland circle, and wherein said X-ray blocking plate blocks parts of at least one of incident X-rays going from a point X-ray source toward the analyzing crystal and X-rays diffracted by the analyzing crystal toward the X-ray detector.

3. A wavelength-dispersive X-ray spectrometer of a straight moving ray-collection type as set forth in claim 1 or 2, wherein said limitation means is made of an X-ray blocking plate made to upstand from an end of a crystal support member supporting the analyzing crystal in the direction of angular dispersion of the crystal toward the center of the Rowland circle in the X-ray spectrometer or toward the center of curvature of the curved analyzing crystal, and wherein said X-ray blocking plate blocks parts of at least one of incident X-rays going from a point X-ray source toward the analyzing crystal and X-rays diffracted by the analyzing crystal toward the X-ray detector.

4. A wavelength-dispersive X-ray spectrometer of a straight moving ray-collection type as set forth in claim 1 or 2, wherein said limitation means is made of an X-ray blocking plate made to upstand perpendicularly to a plane defined by the Rowland circle in the X-ray spectrometer and parallel to a straight line which passes through the center of the analyzing crystal and through the center of the Rowland circle from an end of a crystal support member supporting the analyzing crystal in the direction of angular dispersion of the crystal, and wherein said X-ray blocking plate blocks parts of at least one of incident X-rays going from a point X-ray source toward the analyzing crystal and X-rays diffracted by the analyzing crystal toward the X-ray detector.

5. A wavelength-dispersive X-ray spectrometer of a straight moving ray-collection type as set forth in claim 1 or 2, wherein
(A) said limitation means has an X-ray blocking plate disposed at an end of a crystal support member for the curved analyzing crystal in the direction of angular dispersion of the analyzing crystal,
(B) a part of said X-ray blocking plate covers an appropriate, substantially rectangular region of an end portion of the surface of the analyzing crystal, (C) a front-end portion of the X-ray blocking plate is made to upstand toward the center of the Rowland circle in the X-ray spectrometer or toward the center of curvature of the curved analyzing crystal, and (D) the upstanding portion of the X-ray blocking plate blocks parts of at least one of incident X-rays going from a point X-ray source toward the analyzing crystal and X-rays diffracted by the analyzing crystal toward the X-ray detector.

6. A wavelength-dispersive X-ray spectrometer of a straight moving ray-collection type as set forth in claim 1 or 2, wherein (A) said limitation means has an X-ray blocking plate disposed at an end of a crystal support member for the curved analyzing crystal in the direction of angular dispersion of the analyzing crystal, (B) a part of said X-ray blocking plate covers an appropriate, substantially rectangular region of an end portion of the surface of the analyzing crystal, (C) a front-end portion of the X-ray blocking plate is made to upstand perpendicularly to a plane defined by the Rowland circle in the X-ray spectrometer and parallel to a straight line passing through the center of the analyzing crystal and through the center of the Rowland circle, and (D) the upstanding portion of the X-ray blocking plate blocks parts of at least one of incident X-rays going from a point X-ray source toward the analyzing crystal and X-rays diffracted by the analyzing crystal toward the X-ray detector.

7. A wavelength-dispersive X-ray spectrometer of a straight moving ray-collection type as set forth in claim 1 or 2, wherein said curved analyzing crystal is a Johann crystal having a spherically-curved concave surface having a curvature equal to the diameter of the Rowland circle in the direction of angular dispersion on the lattice plane of the analyzing crystal and in a direction perpendicular to the direction of angular dispersion, and wherein the portion of the X-ray blocking plate which upstands from an end of a crystal support member supporting the spherically-curved Johann crystal in the direction of angular dispersion of the crystal toward the inside of the Rowland circle is substantially rectangular in shape.

8. A wavelength-dispersive X-ray spectrometer of a straight moving ray-collection type as set forth in claim 1 or 2, wherein the height of said X-ray blocking plate upstanding from an end of a crystal support member supporting the analyzing crystal toward the inside of the Rowland circle such that a region contributing to diffraction is set based on data indicating incident angle error of X-rays incident on the surface of the analyzing crystal.

9. A wavelength-dispersive-X-ray spectrometer of a straight moving ray-collection type as set forth in claim 1 or 2, wherein said curved analyzing crystal is an analyzing element made of a layered synthetic microstructure having a lattice spacing of less than 2 nm, and wherein said limitation means is mounted integrally with the analyzing element of the layered synthetic microstructure.

* * * * *